United States Patent [19]
Yates et al.

[11] Patent Number: 5,508,039
[45] Date of Patent: *Apr. 16, 1996

[54] CONTROLLED TRANSDERMAL ADMINISTRATION OF MELATONIN

[75] Inventors: F. Eugene Yates, Pacific Palisades; Lina T. Taskovich, Palo Alto; Su I. Yum, Los Altos; Nieves M. Crisologo, Sunnyvale, all of Calif.

[73] Assignee: ALZA Corporation, Palo Alto, Calif.

[*] Notice: The term of this patent shall not extend beyond the expiration date of Pat. No. 5,284,660.

[21] Appl. No.: 211,786

[22] PCT Filed: Oct. 16, 1992

[86] PCT No.: PCT/US92/08919

§ 371 Date: Jun. 13, 1994

§ 102(e) Date: Jun. 13, 1994

[87] PCT Pub. No.: WO93/07870

PCT Pub. Date: Apr. 29, 1993

Related U.S. Application Data

[63] Continuation-in-part of Ser. No. 779,215, Oct. 18, 1991, abandoned.

[51] Int. Cl.$^6$ ........................................ A61F 13/00
[52] U.S. Cl. ........................ 424/448; 424/447; 424/449
[58] Field of Search ..................... 424/447–448

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |

(List continued on next page.)

FOREIGN PATENT DOCUMENTS

| | | | |
|---|---|---|---|
| 420064A2 | 4/1991 | European Pat. Off. | C07C 233/23 |
| 38856 | 7/1991 | European Pat. Off. | A61K 31/40 |
| WO8700432 | 7/1985 | WIPO | A61K 31/40 |
| WO8901472 | 2/1989 | WIPO | C07D 209/14 |
| WO8904659 | 6/1989 | WIPO | A61K 31/40 |
| WO9014084 | 11/1990 | WIPO | A61K 31/40 |

OTHER PUBLICATIONS

Arendt et al. (1987) Ergonomics 30:1379–1393.
Anton–Tay et al. (1971) Life Sciences 10:841–850.
Wirz–Justice et al. (1990) J. Psychiat. Res. 24(2):129–137.
Arendt et al. (1988) Lancet pp. 722–773.
Folkard et al. (1990) Neuroscience Lett. 113:193–198.
Sack et al., (1987) in, "Temporal Disorder in Human Oscillatory systems," Eds. L. Rensing et al., Springer–Verlag, Heidelberg, pp. 219–224.
Sack and Lewy (1988) Am. Psychiatric Assoc. 141 Ann. Meeting, Montreal, Quebec.
Waldhouser et al. (1990) Psychopharmacology 100:222–226.
Arendt et al. (1991) Lancet 337:1121–1124.
Barch et al. (1991) Cancer 67:1681–1684.

(List continued on next page.)

*Primary Examiner*—D. Gabrielle Phelan
*Attorney, Agent, or Firm*—Michael J. Rafa; Steven F. Stone; Edward L. Mandell

[57] ABSTRACT

The present invention is directed to the transdermal administration of melatonin together with a suitable permeation enhancer. The invention includes a transdermal drug delivery device (10) comprising a matrix (12) adapted to be placed in melatonin- and permeation enhancer-transmitting relation with the skin site (18). The matrix (12) contains sufficient amounts of a permeation enhancer and of melatonin, in combination, to continuously administer to the skin (18) for a predetermined period of time the melatonin to provide an effective therapeutic result. The invention is also directed to a method for the transdermal administration of a therapeutically effective amount of melatonin together with a skin permeation-enhancing amount of a suitable permeation enhancer. The invention further includes methods for time- and rate-patterned transdermal delivery of melatonin to simulate the natural circadian rhythmic profile of melatonin in mammals.

33 Claims, 3 Drawing Sheets

U.S. PATENT DOCUMENTS

| | | | |
|---|---|---|---|
| 4,031,894 | 6/1977 | Urquhart et al. | 128/268 |
| 4,144,317 | 3/1979 | Higuchi et al. | 424/21 |
| 4,201,211 | 5/1980 | Chandrasekaran et al. | 128/268 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,435,180 | 3/1984 | Leeper | 604/896 |
| 4,559,222 | 12/1985 | Enscore et al. | 424/28 |
| 4,573,995 | 3/1986 | Cheng et al. | 604/896 |
| 4,588,580 | 1/1989 | Gale et al. | 424/21 |
| 4,600,723 | 7/1986 | Short et al. | 514/416 |
| 4,645,502 | 2/1987 | Gale et al. | 604/896 |
| 4,654,361 | 3/1987 | Samples et al. | 514/419 |
| 4,665,086 | 5/1987 | Short et al. | 514/416 |
| 4,704,282 | 11/1987 | Campbell et al. | 424/449 |
| 4,746,575 | 5/1988 | Cheng et al. | 428/419 |
| 4,788,062 | 11/1988 | Gale et al. | 424/449 |
| 4,816,258 | 3/1989 | Nedberge et al. | 424/448 |
| 4,849,226 | 7/1989 | Gale | 424/448 |
| 4,855,305 | 8/1989 | Cohen | 514/171 |
| 4,880,826 | 11/1989 | Zisapel et al. | 514/415 |
| 4,908,027 | 3/1990 | Enscore et al. | 604/890.1 |
| 4,943,435 | 7/1990 | Baker et al. | 424/448 |
| 4,945,103 | 7/1990 | Cohen | 514/419 |
| 4,948,103 | 7/1990 | Cohen | 514/419 |
| 5,049,387 | 9/1991 | Amkraut | 424/448 |
| 5,242,941 | 9/1993 | Lewy | 514/416 |
| 5,284,660 | 2/1994 | Lee | 424/449 |

OTHER PUBLICATIONS

Parry et al. (1990) Arch. Gen. Psychiatry 47:1139–1146.

Yen et al. (1990) Arch. Gen. Psych. 47:1139–1146.

Wurtman et al. (1990) Forensic Science Interntl. 45:171–180.

Reiter (1981) Endocr. Rev. 1:109–131.

Nittman et al. (1983) Endocrinology 113:2276–2283.

Arendt (1986) Oxford Reviews of Reproductive Biology 8:266–320.

Frohn et al. (Life Sciences, vol. 27, pp. 2043–2046, Pergamon Press.

Clemens et al. (J. Neural Transm., 1986, (suppl.) 21:451–459.

"Transdermal Drug Delivery: Problems and Possibilities", V. M. Knepp et al., CRC Critical Reviews and Therapeutic Drug Carrrier Systems, vol. 4, Issue 1, 1987.

CONTROLLED TRANSDERMAL ADMINISTRATION OF MELATONIN

This application is a 371 of PCT/US92/08919, filed Oct. 16, 1992, which is a continuation-in-part of parent case U.S. Ser. No. 07/779,215, filed Oct. 18, 1991, now abandoned.

FIELD OF THE INVENTION

This invention relates the efficacious and safe, controlled transdermal administration of melatonin and related compounds for systemic hypnotic and soporific effects in the treatment of insomnias of several kinds.

BACKGROUND OF THE INVENTION

Melatonin (N-acetyl-5-methoxytryptamine) is a hormone synthesized and secreted by the pineal gland. The exact function of the hormone in adult human beings has not been determined. In healthy young adults, melatonin is secreted as a broad pulse during nighttime sleep in the total amount of approximately 25–30 μg per night, producing peak plasma concentrations of approximately 70 pg/ml, occurring at approximately 0200 h. Melatonin is secreted into the blood stream and possibly also into cerebrospinal fluid (CSF) simultaneously. The CSF/plasma concentration ratio is 1.0 or less. The terminal plasma elimination half-life is approximately 45 minutes; volume of distribution is approximately 40 liters; and the metabolic clearance of melatonin is approximately 1 liter per minute. The melatonin circadian (~ 24 hr) rhythm is thought to be driven by the same central nervous system oscillator that drives the daily rhythms of cortisol, urine volume, and core temperature (Shanahan and Czeisler, 1991), The relationship of the melatonin cycle to the activity/rest (sleep) cycle is not clear, but melatonin may organize the normal sleep pattern.

Melatonin has been administered to human beings orally and intranasally. It is readily absorbed through the gastrointestinal tract. The liver inactivates as much as 99% of the absorbed melatonin on the first-pass. Thus, the oral route of administration is inefficient and erratic.

Oral melatonin has been given to human beings to treat the phenomenon of "jet lag" following airplane trips associated with a change in time zones (Arendt et al. (1987) *Ergonomics* 30:1379–1393); U.S. Pat. Nos. 4,600,723 and 4,665,086). It has been given to patients with Parkinson's disease (Anton-Tay et al. (1971) *Life Sciences* 10:841–850), epilepsy (Anton-Tay et al., ibid.), or seasonal affective disorders (Wirz-Justice et al. (1990) *J. Psychiat. Res.* 24(2):129–137). It has been tried as a sleep-wake organizer in desynchronized blind persons (Arendt et al. (1988) *Lancet* pp 772–773; Folkard et al. (1990) *Neuroscience Lett.* 113:193–198; Sack et al., (1987) in, "Temporal Disorder in Human Oscillatory Systems", Eds. L. Rensing et al., Springer-Verlag, Heidelberg, pp 219–224; Sack and Lewy (1988) *Am. Psychiatric Assoc.* 141 Ann. Meeting, Montreal, Quebec). Improved timing of sleep cycles resulted. Oral melatonin has been given to insomniacs (Waldhouser et al. (1990) *Psychopharmacology* 100:222–226; Arendt et al. (1991) *Lancet* 337:1121–1124). Melatonin reduced the time awake before sleep onset and diminished sleep latency and number of awakenings. Overall sleep efficiency was increased, and mood, drive, alertness, and reaction time were improved the next day. Most of the published studies are consistent with the assumption that melatonin has mild sedative and hypnotic properties and may be a natural, sleep-inducing and sleep-organizing signal in humans. In addition, melatonin has been reported to lower intraocular pressure in glaucoma, to inhibit breast cancer (U.S. Pat. No. 4,855,305; Barch et al. (1991) *Cancer* 67:1681–1684), to be useful in the treatment of premenstrual depression (U.S. Pat. No. 4,945,103; Parry et al. (1990) *Arch. Gen. Psychiatry* 47:1139–1146; Yen et al. (1990) *Arch. Gen. Psych.* 47:1139–1146), for effecting contraception in humans (PCT Appln. WO 90/14084), and to prevent sudden infant death syndrome (Wurtman et al. (1990) *Forensic Science Interntl.* 45:171–180). Melatonin appears to be useful in animal husbandry by, for example, regulating the reproductive behavior of animal seasonal breeders (Reiter (1981) *Endocr. Rev.* 1:109–131; Nittman et al. (1983) *Endocrinology* 113:2276–2283; Arendt (1986) *Oxford Reviews of Reproductive Biology* 8:266–320) and regulating fur coat development in animals with seasonal variation.

Numerous analogs, homologs, agonists, antagonists and other compounds related to melatonin are known in the art, representatives of which are disclosed in, for example, U.S. Pat. No. 4,880,826, WO 87/00432, WO 89/01472, WO 89/04659, WO 90/14084, and EP 420 064, and by Frohn et al. (*Life Sciences*, Vol. 27, pp 2043–2046, Pergamon Press) and Clemens et al. (*J. Neural Transm.*, (1986) (supp.) 21:451–459).

The transdermal route of administration for drugs and other biologically active agents ("agents") has been proposed for a wide variety of systemically acting and locally acting agents on either a rate-controlled or non rate-controlled basis and is described in numerous technical publications and patents, such as U.S. Pat. Nos. 3,598,122; 3,598,123; 3,731,683; 3,797,494; 4,031,894; 4,201,211; 4,286,592; 4,314,557; 4,379,454; 4,435,180; 4,588,580; 4,645,502; 4,704,282; 4,788,062; 4,816,258; 4,908,027; 4,943,435; and 5,004,610. The disclosures of the above patents are incorporated herein by reference.

When first investigated in depth in the late 1960's, the transdermal route of administration of active agents appeared to offer many advantages, particularly with respect to agents that had short half-lives and a high degree of first-pass metabolism by the liver when orally administered. Presentation of the agent through the skin directly into the blood stream would eliminate "first-pass" metabolism of orally administered agents, which excludes the oral portal for some agents or requires extremely large oral doses for others.

In spite of intensive research and development activities by most of the major pharmaceutical companies on the potential candidates for transdermal administration, only six drugs are presently commercially available in the United States in the form of transdermal drug delivery devices: nitroglycerin, scopolamine, clonidine, estradiol, nicotine and fentanyl. This set is small because of difficulties inherent in the barrier properties of skin [see "Transdermal Drug Delivery: Problems and Possibilities", V. M. Knepp et al., *CRC Critical Reviews and Therapeutic Drug Carrier Systems*, Vol. 4, Issue 1, (1987)].

The skin is a complex structure that performs its barrier function in several ways:

1. As a physical barrier having a relatively low permeability for most substances;
2. As a sensory organ;
3. As a metabolizing organ capable of converting some topically applied substances into metabolites.

Thus, the transdermal route of administration, rather than being useful for every short half-life agent of high potency, has been found to be applicable only to a few agents possessing certain characteristics. The most significant of these considerations are:

1. Skin permeability. The permeability of the agent through the skin must be sufficiently high so that it can be administered at therapeutically effective rates through an area of skin no greater than approximately 100 cm$^2$ and preferably no greater than 50 cm$^2$. The person-to-person variation in skin permeability at similar sites should also be relatively small.

2. Skin binding. The skin beneath a transdermal delivery device has the potential capability of binding or dissolving a certain amount of agent. The amount of agent so bound must be supplied to the skin before the agent can be delivered into the blood stream at therapeutically effective rates. If large amounts of the agent are bound in the skin, significant delays in the onset of therapeutic effect ("lag time") will be observed, as well as corresponding delays in termination of effect upon removal of the device. Skin binding is not related to skin permeability. Agents that are highly permeable may also be highly bound, causing a lag time sufficiently long as to render them unsuitable for their intended use.

3. Irritation. The skin reacts to many topically applied substances, particularly those maintained under occlusion, by blistering or reddening accompanied by unpleasant burning, itching, and stinging sensations. There is a wide inter-subject variation in susceptibility to irritation. An agent must be minimally irritating in a large percentage of the potential patient population in order to be suitable for safe and effective transdermal administration.

4. Sensitization. Sensitization is an allergic reaction that is induced when an agent is first applied to the skin and is elicited upon continued exposure, which may occur immediately or after a long period of seemingly harmless exposure. The sensitization may be local, elicited by topical exposure, which manifests itself as contact dermatitis accompanied by blistering, itching, reddening, and burning at the site of application. More seriously, the sensitization may be systemic, elicited by topical application but manifesting itself by more general allergic reactions at sites other than the site of application. Most seriously, the systemic sensitization may be elicited by oral or intravenous administration of the drug. If the latter occurs, the patient will be unable to take the drug by any route of administration.

There is a wide variation in allergic response among individuals as well as between sexes, races, and skin types. It is obvious that a useful transdermal agent must be minimally sensitizing in a large percentage of the potential patient population.

5. Pharmacokinetic properties. The elimination half-life of an agent is the time after administration that half of the amount administered has been eliminated from the body. Blood concentrations of agents continuously administered at constant rates will continue to increase for approximately five half-lives before steady-state, constant blood concentrations are achieved. It is usually desirable that an agent have a relatively short half-life to be suitable for controlled, transdermal administration. When half-lives of agents determined from intravenous administration are compared with half-lives determined from transdermal administration, the transdermal half-lives are generally longer, but there can be wide variation in half-life among individuals based upon such factors as age, sex, health, and body type. The transdermal half-lives of most agents have not been determined.

6. Pharmacodynamic properties. Constant blood levels may not produce the optimal therapeutic effects. For example, a therapeutic effect may only be observed at the peak blood concentration obtained from bolus dosing, but the peak concentration cannot be maintained because of side effects associated therewith. Also, continuous administration of many agents produces tolerance. Other cases may require either some agent-free interval or continually varying doses of the agent.

7. Potency. Although a high potency is required for feasibility of transdermal administration of an agent, it is possible for an agent to be too potent. As potency increases, lower blood concentrations are required and much smaller total quantities are administered. Because of the normal inter-individual variations in skin permeability, it may not be possible to control precisely the dose a patient receives, and for potent agents with narrow "therapeutic windows," this uncertainty can be hazardous. Fortunately, in the present case, melatonin is relatively non-toxic.

8. Metabolism. One of the perceived advantages of transdermal administration was that it avoided the "first-pass" metabolism of the agent by the liver which is associated with oral administration. It has now been recognized, however, that the skin, not the liver, is the largest metabolizing organ in the body. Thus, although first-pass metabolism which occurs after an orally adjusted agent enters the blood stream can be avoided, skin metabolism, which occurs before the agent enters the blood stream, must be dealt with. Skin metabolism is capable of creating metabolites which are inert, toxic or comparable in biological activity to that of the agent. An agent, to be suitable for transdermal administration, must have the metabolic properties that are consistent with its therapeutic use on continuous administration.

The above summarizes the primary characteristics recognized to date that affect suitability of an agent for transdermal administration. There are undoubtedly others, some of which have not yet been recognized. In order for an agent to be suitable for transdermal administration it must possess the right combination of all of these characteristics, a combination which, as illustrated by the very few drugs which are now known to be suitable for administration from transdermal delivery devices, is quite rare and unpredictable.

SUMMARY OF THE INVENTION

According to the present invention, it has been discovered that melatonin may be safely and efficaciously administered transdermally and in a controlled manner. Methods for the transdermal delivery of melatonin and delivery devices for effecting the same, which are suitable for the administration of melatonin through mucosa and intact skin, are provided.

More particularly, the present invention is directed to the transdermal administration of melatonin, together with a suitable permeation enhancer. The invention includes a transdermal drug delivery device containing sufficient amounts of permeation enhancer and of melatonin, in combination, to provide systemic administration of melatonin through the skin for a predetermined period of time for the melatonin to provide an effective therapeutic result.

The invention is also directed to a method for the transdermal administration of a therapeutically effective amount of melatonin together with a skin permeation-enhancing amount of a suitable permeation enhancer. The invention further includes methods for time- and rate-patterned transdermal delivery of melatonin to simulate the natural circadian rhythmic profile of melatonin in mammals.

While the preferred active agent according to the present invention is melatonin itself, the invention also includes analogs, homologs, agonists, antagonists and other compounds related to melatonin. The term "melatonin" is used herein to designate both the actual melatonin and the related compounds thereof.

DETAILED DESCRIPTION OF THE INVENTION AND PREFERRED EMBODIMENTS

According to the present invention, it has been found that melatonin may be administered to the human body in a therapeutically effective amount via the transdermal route when it is co-administered with a suitable permeation enhancer. Therapeutic blood levels from 20 pg/ml to 1,000 pg/ml can be obtained from administration rates in the range of 1 mg/hr to 100 mg/hr. Representative skin fluxes of melatonin through living human skin are in the range of 0.05 $mg/cm^2/hr$ to 10 $mg/cm^2/hr$, depending on the permeation enhancer. The plasma terminal half-life of melatonin administered transdermally is in the range of 1 to 2 hours. Therapeutic blood levels can be achieved within approximately 2 hours, and peak blood concentrations are achieved at about 4–6 hours when the system is worn for 4–6 hours. The range of desired and achievable system fluxes of melatonin, arriving through the skin from a limited area, is 0.025–1.0 mg over a period of 4–8 hours. The system application is easily adapted for shorter or longer duration treatments, but generally 6 hours is the nominal duration for treatment of most insomnias.

Typical transdermal delivery devices are described in U.S. Pat. Nos. 3,598,122; 3,598,123; 4,286,592; 4,314,557; 4,379,454; 4,559,222; 4,573,995; and 4,849,226, for example. All of these are incorporated herein by reference. The co-administration of melatonin and a permeation enhancer as disclosed herein can be accomplished by using transdermal devices of these kinds.

Because of the wide variation in skin permeability from individual and from site to site on the same body, it may be preferable that melatonin and the permeation enhancer be administered from a rate-controlled transdermal delivery device. Rate control can be obtained either through a rate-controlling membrane or adhesive or through the other means disclosed in the patents noted above.

A certain amount of melatonin will bind to the skin, and it is accordingly preferred that the skin-contacting layer of the device include this amount of the agent as a loading dose.

Examples of suitable transdermal delivery devices are illustrated in FIGS. 1, 2, 3 and 4. In the drawings, the same reference numbers are used throughout the different figures to designate the same or similar components. The figures are not drawn to scale.

Figure 1:
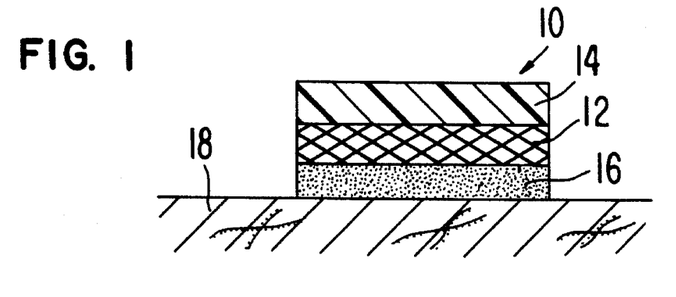
FIG. 1 is a cross-section through a schematic perspective view of one embodiment of transdermal therapeutic devices according to this invention.

In FIG. 1, transdermal delivery device 10 comprises a reservoir 12 containing both melatonin and a suitable permeation enhancer. Reservoir 12 is preferably in the form of a matrix containing the drug and enhancer dispersed therein. Reservoir 12 is sandwiched between a backing layer 14, which is impermeable to both the drug and the enhancer, and an in-line contact adhesive layer 16. The device 10 adheres to the surface of the skin 18 by means of the adhesive layer 16. The adhesive layer 16 may optionally contain enhancer and/or drug. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16.

Figure 2:
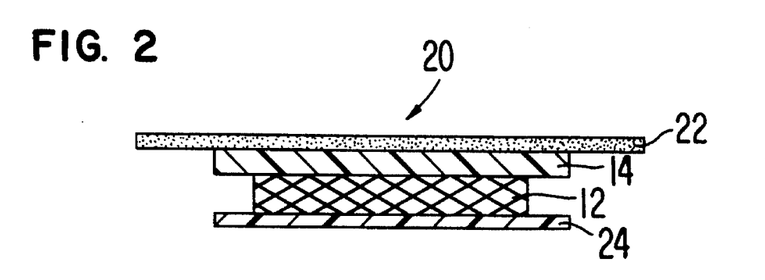
FIG. 2 is a cross-section through another embodiment of a transdermal therapeutic device according to this invention.

Alternatively, as shown in FIG. 2, transdermal therapeutic device 20 may be attached to the skin or mucosa of a patient by means of an adhesive overlay 22. Device 20 is comprised of a melatonin- and permeation enhancer-containing reservoir 12 which is preferably in the form of a matrix containing the drug and the enhancer dispersed therein. An impermeable backing layer 14 is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. This is true, for example, where the drug/enhancer reservoir contains a material (such as, for example, an oily surfactant permeation enhancer) which adversely affects the adhesive properties of the in-line contact adhesive layer 16. Impermeable backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

Figure 3:
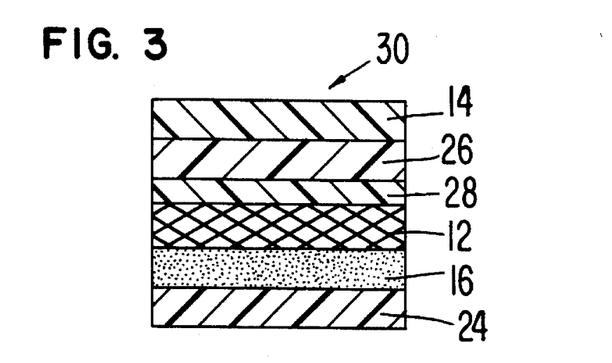
FIG. 3 is a cross-section through yet another embodiment of a transdermal therapeutic device according to this invention.

In FIG. 3, transdermal delivery device 30 comprises a melatonin- and permeation enhancer-containing reservoir ("drug reservoir") 12 substantially as described with respect to FIG. 1. Permeation enhancer reservoir ("enhancer reservoir") 26 comprises permeation enhancer dispersed throughout and is substantially free of any undissolved melatonin. Enhancer reservoir 26 is preferably made from substantially the same matrix as is used to form drug reservoir 12. A rate-controlling membrane 28 for controlling the release rate of the permeation enhancer from enhancer reservoir 26 to drug reservoir 12 is placed between the two reservoirs. A rate-controlling membrane (not shown in FIG. 3) for controlling the release rate of the enhancer from drug reservoir 12 to the skin may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate and ethylene vinyl acetate copolymers.

Superimposed over the permeation enhancer reservoir 26 of device 30 is an impermeable backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12 which contains the melatonin and permeation enhancer and bears on its surface distant from backing member 14 a rate-controlling membrane 28 for controlling the release of melatonin and/or permeation enhancer from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

Figure 4:
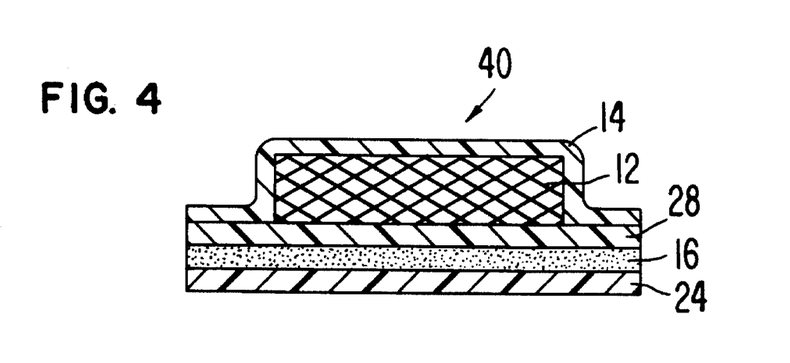
FIG. 4 is a cross-section through yet another embodiment of a transdermal therapeutic device according to this invention.

In an alternative embodiment of device 40 of FIG. 4, reservoir 12 contains the permeation enhancer only and is substantially free of melatonin. The melatonin and an additional amount of permeation enhancer are present in adhesive layer 16 which acts as a separate reservoir.

The melatonin and the permeation enhancer can be coextensively administered to human skin or mucosa by direct application to the skin or mucosa in the form of an ointment, gel, cream or lotion, for example, but are preferably administered from a skin patch or other known transdermal delivery device which contains a saturated or unsaturated formulation of the drug and the enhancer. The formulation may be aqueous or non-aqueous based. The formulation should be designed to deliver the melatonin and the permeation enhancer at the necessary fluxes. Aqueous formulations typically comprise water or water/ethanol and about 1–2 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with both the melatonin and the permeation enhancer and any other components in the formulation.

The reservoir matrix should be compatible with the drug, the permeation enhancer and any carrier therefor. The term "matrix" as used herein refers to a well-mixed composite of ingredients fixed into shape. When using an aqueous-based formulation, the reservoir matrix is preferably a hydrophilic polymer, e.g., a hydrogel. When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference.

A typical laminated system would comprise a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 28% to 60% VA. Polyisobutylene/oil polymers containing from 4–25% high molecular weight polyisobutylene and 20–81% low molecular weight polyisobutylene with the balance being an oil such as mineral oil or polyisobutynes may also be used as the matrix material.

The aforementioned patents describe a wide variety of materials which can be used for fabricating the various layers or components of the transdermal melatonin delivery devices according to this invention. This invention therefore contemplates the use of materials other than those specifically disclosed herein, including those which may hereafter become known to the art to be capable of performing the necessary functions.

The amount of melatonin present in the therapeutic device and required to achieve an effective therapeutic result depends on many factors, such as the minimum necessary dosage of the drug for the particular indication being treated; the solubility and permeability of the matrix, of the adhesive layer and of the rate-controlling membrane, if present; and the period of time for which the device will be fixed to the skin. The minimum amount of melatonin is determined by the requirement that sufficient quantities of drug must be present in the device to maintain the desired rate of release over the given period of application. The maximum amount for safety purposes is determined by the requirement that the quantity of melatonin present cannot exceed a rate of release that reaches toxic levels. Melatonin is relatively non-toxic. An $LD_{50}$ has been determined in mice at 1375 mg/kg by intraperitoneal administration and 180 mg/kg by intravenous administration. These are extraordinarily high levels. In the human being the natural twenty-four hour secretion in 0.3 μg/kg. During daylight hours, the secretion rate is essentially zero.

When a constant drug delivery rate is desired, the melatonin is normally present in the matrix or carrier at a concentration in excess of saturation, the amount of excess being a function of the desired length of the drug delivery period of the system. The melatonin may, however, be present at a level below saturation without departing from this invention as long as the drug is continuously administered to the skin or mucosa site in an amount and for a period of time sufficient to provide the desired therapeutic rate and delivery profile of melatonin delivery.

The permeation enhancer is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

The permeation enhancer useful in the present invention is selected from those compounds which are compatible with melatonin and which provide enhanced skin permeation to melatonin when it is administered together with the drug to the skin of a user. Such permeation enhancers can be selected from, but are not limited to, $C_{2-4}$ alcohols such as ethanol and isopropanol, polyethylene glycol monolaurate, polyethylene glycol-3-lauramide, dimethyl lauramide, sorbitan trioleate, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and tri-glycerides of fatty acids. Fatty acids are, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a preferred embodiment, the permeation enhancer is glycerol monooleate or glycerol monolinoleate, more preferably glycerol monooleate. Combinations of two or more permeation enhancers or of permeation enhancers with bile salts are also contemplated.

In addition to melatonin and a suitable permeation enhancer, which are essential to the invention, the matrix or carrier may also contain dyes, pigments, inert fillers, excipients and other conventional components of pharmaceutical products or transdermal devices known to the art.

In the present invention, melatonin is delivered at a therapeutically effective rate (that is, a rate that provides a desired therapeutic effect) and the permeation enhancer is delivered at a permeation-enhancing rate (that is, a rate that provides increased permeability of the application site to the melatonin) for a predetermined time period and in the required delivery pattern.

A preferred embodiment of the present invention comprises a method of treating any disorder in which it is therapeutic to mimic or inhibit melatonin function or influence circadian rhythms by administering a therapeutically effective amount of one or more of the compounds of the present invention to a patient suffering from such disorder.

Another preferred embodiment of the present invention comprises a method of treating chronobiological disorders, e.g., seasonal affective disorders (SAD), sleep disorders, and symptoms such as drowsiness and fatigue that are associated with disturbances in sleep/wake cycles (e.g., jet lag, workers on night shifts, etc.) by administering a therapeutically effective amount of one or more of the compounds of the present invention to a patient suffering from one or more of such chronobiological disorders.

Another preferred embodiment of the present invention comprises a method of treating various psychiatric disorders related to altered melatonin function or influenced by melatonin and circadian rhythms, e.g., affective disorders (mania and depression), alcoholism, and stress by administering a therapeutically effective amount of one or more of the compounds of the present invention to a patient suffering from one or more of such psychiatric disorders.

Another preferred embodiment of the present invention comprises a method of treating or inducing various endocrine-related conditions attributed to altered melatonin function or influenced by melatonin and biological rhythms, particularly relating to regulation of reproductive maturation and function, e.g., idiopathic delayed puberty, premature labor, and antifertility, by administering a therapeutically effective amount of one or more of the compounds of the present invention to a patient suffering from or desiring to induce one or more of such endocrine-related conditions. In addition, it is thought that the compounds of the invention can be used to treat or prevent glaucoma by lowering the intraocular pressure and to manipulate body weight by administering an effective amount of one or more of the compounds herein.

A further preferred embodiment of the present invention comprises a method for manipulating the breeding and fur-bearing cycles in animals by administering to such animal an effective amount of one or more of the compounds of the present invention.

A further preferred embodiment of the present invention comprises a method for restoring the youthful natural pattern or profile of excretion of specific cyclical hormones which are affected by the levels of melatonin in the body, such as growth hormone, calcitonin, and in males, testosterone.

In a presently particularly preferred embodiment, melatonin is useful as a sleep-producing agent for use by elderly persons who have fragmented sleep.

Figure 5:
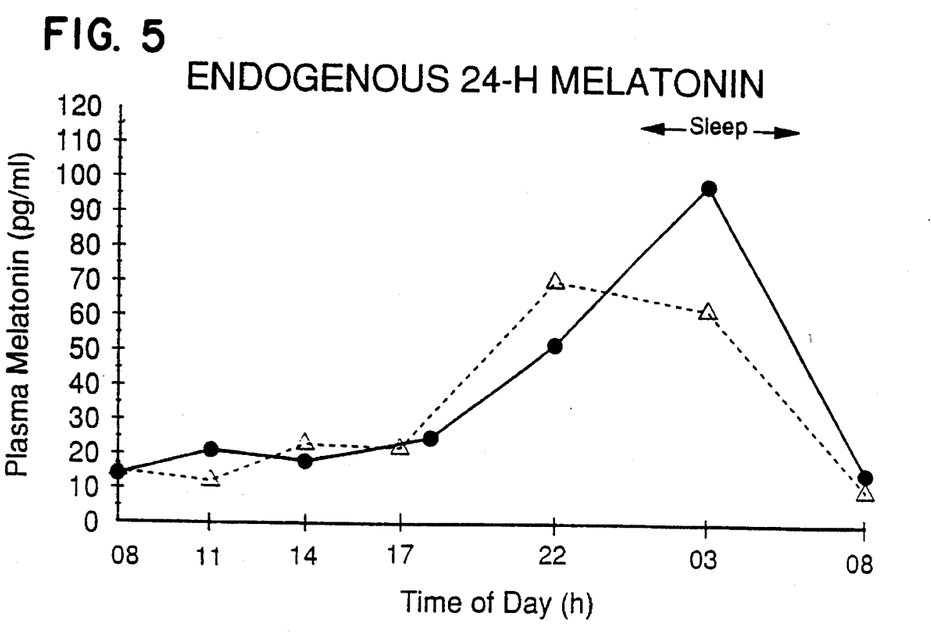
FIG. 5 shows the baseline melatonin plasma concentrations of a young woman over two separate days.

To be useful as a hypnotic, melatonin should be present in plasma at levels above 20 pg/ml for about 5 or 6 hours during the normal sleep cycle of the user, and preferably at levels which approximate the natural bell-shaped curve distribution of melatonin in the body. FIG. 5 presents the natural plasma levels of melatonin in a healthy, normal individual and illustrates the bell curve-shaped distribution. To achieve this result, the melatonin is delivered at a therapeutic rate of at least about 0.1 µg per hour, but typically of at least 2 µg/hr, and more typically at about 10 µg/hr to about 200 µg/hr, for the treatment period, usually about 4 to 6 hours, after which melatonin delivery is discontinued. The delivery device containing the melatonin and a permeation enhancer is placed on a user at a time prior to the bedtime of the user such that the device is delivering melatonin in a therapeutically effective amount to the user when the user goes to bed.

To provide the proper effect, or in other words to provide the desired bell-shaped curve, it is necessary that, at the end of the period of melatonin delivery, the supply of melatonin from the therapeutic device is "shut off" or discontinued so that melatonin s will clear from the body. Thus, in a departure from previous uses of transdermal drug delivery, steady-state delivery of melatonin is not desired.

The melatonin supply from a device of the present invention may be discontinued in one of several ways. The first is to physically remove the device after about 4–5 hours. However, since this usually will require that the user wakes up, it defeats the purpose of providing an uninterrupted period of sleep. An alternative, which is a preferred embodiment of the invention, is to provide means in the delivery device itself for shutting off the supply of drug after a predetermined period of time, usually after about 1–6 hours and preferably after about 4–5 hours, depending on the user's need and variations in skin binding and systemic clearance of melatonin.

This may be accomplished by limiting the amount of melatonin present in the delivery device to only that amount which will be delivered at the therapeutic rate for the predetermined time period. For example, where the drug is delivered from the system at a rate of 5 µg/hr and the desired period of delivery is 5 hours, the total amount of melatonin present in the device will be about 25 µg. Thus, after 5 hours, systemic delivery of melatonin will cease and the amount of melatonin in the blood plasma will decrease as the melatonin is cleared from the body. In such cases where there is a limited amount of melatonin present in the device, it is usually desired that the permeation enhancer present in the device be in an amount in excess of that which is necessary to provide increased permeability to the melatonin that is present. Where there is a limited amount of melatonin and an excess of permeation enhancer in the transdermal device, the device of FIG. 3 or FIG. 4 is preferred, having a separate permeation enhancer reservoir containing an excess of enhancer. In this way, the melatonin is concentrated near the skin while an adequate permeation enhancer supply is maintained.

Alternatively, means for shutting off the supply of melatonin that enters the body transdermally may be accomplished by limiting the amount of permeation enhancer present in the delivery device, rather than the amount of melatonin. Because melatonin alone has a very low flux through skin, delivery of the drug in therapeutically effective amounts or rates will effectively cease once permeation enhancer is no longer present. In this situation it is not necessary for the drug and permeation enhancer to be separated, so that a transdermal device such as illustrated in FIG. 1 may be used.

In a third alternative, the amounts of both melatonin and permeation enhancer are limited in the delivery device so that after a predetermined period of time systemic melatonin delivery will cease and the amount of melatonin in the body will decline to an undetectable level. A device such as that in FIG. 1 may be used in this embodiment.

The length of time of melatonin presence and the total amount of melatonin in the plasma can be changed following the teachings of this invention to provide different treatment regimens. Thus, they can be controlled by the amount of time during which exogenous melatonin is delivered transdermally to an individual or animal.

The devices of this invention can be designed to effectively deliver melatonin for an extended time period of from several hours up to 7 days or longer. Seven days is generally the maximum time limit for application of a single device because the skin site is adversely affected when occluded for a period greater than 7 days. However, when the indication is to provide uninterrupted sleep, it is only necessary for the device to be applied to the skin during the normal sleep cycle of the user, after which it is removed and discarded.

The transdermal therapeutic devices of the present invention are prepared in a manner known in the art, such as by those procedures, for example, described in the transdermal device patents listed previously herein.

Having thus generally described the invention, the following specific examples describe preferred embodiments thereof.

EXAMPLE 1

Delivery devices according to the present invention were prepared as follows.

EVA 40 (EVA with 40% vinyl acetate) (2.7 g), glycerol monooleate (1.5 g; Myverol® 1899K, Eastman Chemical Products, having a glycerol monooleate content of 61% and a total monoesters content of 93%; "M-GMO") and chloroform (27.0 g) were added together in a vial. The vial was capped (Teflon®-lined) and rotated for 4–6 hours, until the EVA 40 was dissolved. The resulting homogeneous solution was then poured onto a glass plate lined with a siliconized polyester release liner film (siliconized PET). The chloroform was evaporated off until the film was dry. Melatonin (0.35 g; Sigma Chemicals) was then dry blended into 1.98 g of the EVA 40/M-GMO dry film in a rubber mill until homogeneous. The resulting material, having a composition of 15 wt % melatonin, 30 wt % M-GMO and 55 wt % EVA 40, was melt pressed (PHI press) to about 8 mil (0.2 mm) thickness between two sheets of siliconized PET release liner at 60° C. and 10,000 lbs. pressure. The resulting film was heat-laminated to an impermeable backing (Medpar® or Scotchpak®, for example). The drug matrix/impermeable backing laminate was then laminated, on the side opposite the impermeable backing, to an acrylic contact adhesive (2 mil; MSX 1010P, 3M) to provide a monolith with an in-line adhesive. Discs of 19 cm$^2$ size each were punched or die-cut from the laminate to give devices having 55.6 mg of melatonin per device or 2.92 mg of melatonin per cm$^2$.

EXAMPLE 2

The in vitro transdermal melatonin fluxes through the epidermis of nine human skin donors from devices of Example 1 were determined. For each device tested, the drug-releasing adhesive surface was placed against the stratum corneum side of a disc of human epidermis which had been blotted dry just prior to use. The excess epidermis was wrapped around the device so that none of the device edge was exposed to the receptor solution. The device covered with epidermis was attached to the flat side of the Teflon® holder of a release rate rod by wrapping around a square nylon mesh and tied with metal string. The rods were reciprocated in a fixed volume of receptor solution (3% ethanol in distilled water). The entire receptor solution was changed at each sampling time. The temperature of the receptor solution in the water bath was maintained at 35° C.

The in vitro transdermal flux of the devices ranged from 0.5 to 20 µg/cm$^2$-hr (N=27).

EXAMPLE 3

The in vivo blood plasma levels of melatonin in two individuals treated with a device according to Example 1 were determined.

Blood samples were drawn from a 39 year old healthy female over a 24-hour period at two different times two weeks apart, and the concentration of melatonin in the plasma of each sample was determined. These formed the baseline endogenous melatonin concentrations (the control) of the individual, as shown in FIG. 5. One day after the second (last) baseline sampling, one transdermal device according to Example 1, of 19 cm$^2$ size and containing 64 mg of melatonin, was placed by the individual on the lateral abdomen in the morning (8:00 a.m.) and was worn for 4 hours, during which period the endogenous melatonin levels were very low, as determined in the control phase. After 4 hours (noon), the device was removed. Blood samples were drawn before the device was applied and then at intervals over 24 hours after the device was applied. The results are shown in FIG. 6.

Figure 7:
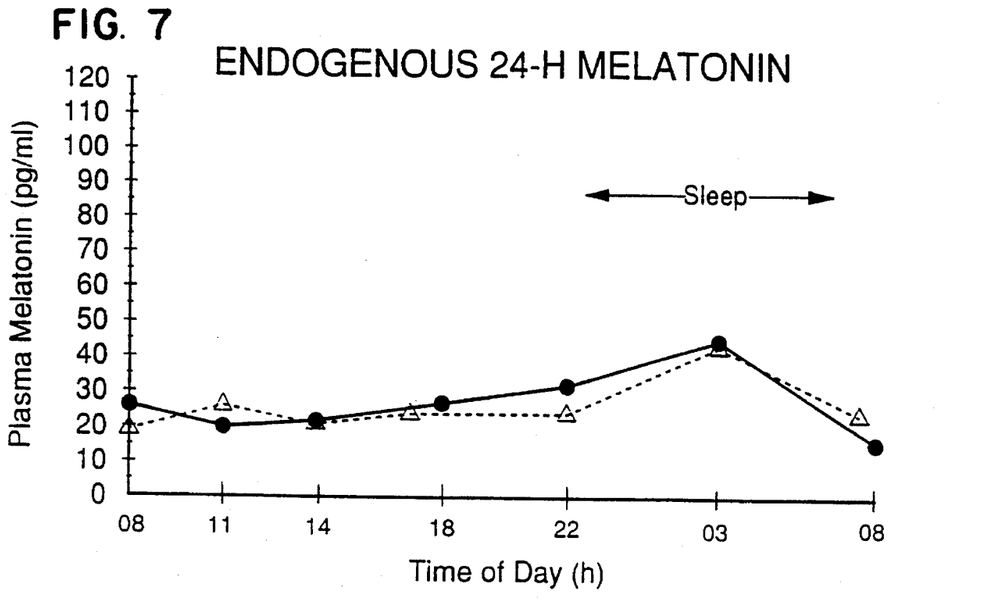
FIGS. 7 and 8 show the plasma melatonin concentrations in another individual (an older man) during baseline monitoring (FIG. 7) and on a day when he wore and then removed a transdermal device according to this invention (FIG. 8).

In the same manner as above, blood samples were drawn from a 63 year old healthy male over a 24-hour period at two different times one week apart, and the concentration of melatonin in the plasma of each sample was determined. These formed the baseline endogenous melatonin concentrations (the control) of the individual, as shown in FIG. 7. Two days after the second (last) baseline sampling, one transdermal device according to Example 1, of 19 cm² size and containing 64 mg of melatonin, was placed by the individual on the lateral abdomen in the morning (8:00 a.m.) and was worn for 4 hours, during which period the endogenous melatonin levels were very low. After 4 hours (noon), the device was removed. Blood samples were drawn before the device was applied and then at intervals over 24 hours after the device was applied. The results are shown in FIG. 8.

Figure 6:
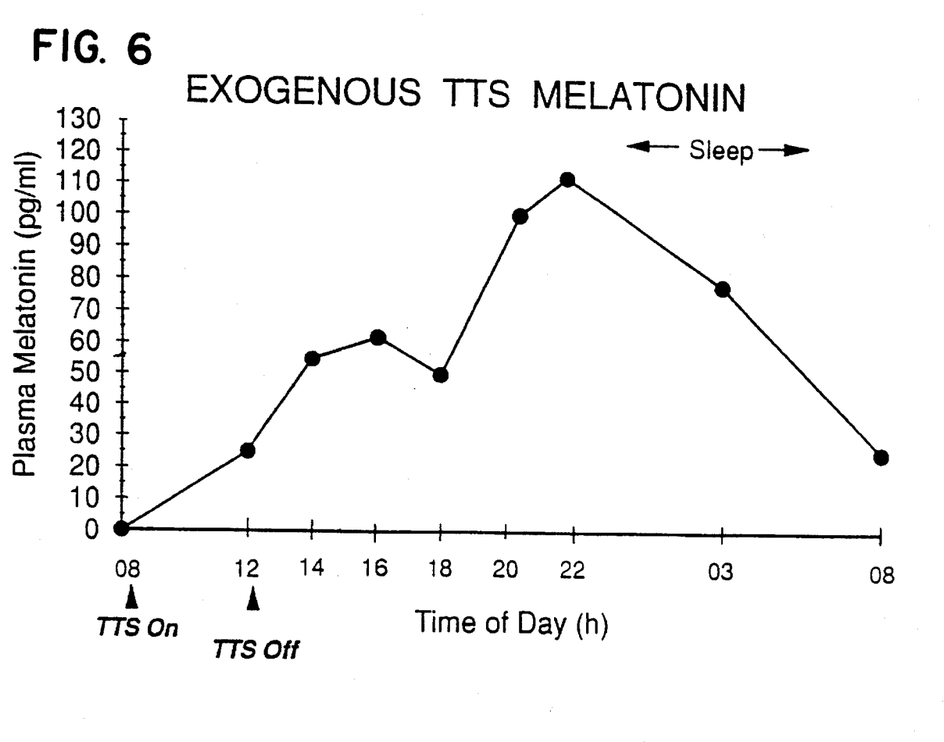
FIG. 6 shows the melatonin plasma concentration of the same individual as in FIG. 5 on a different day when she wore and then removed a transdermal device according to this invention.
Figure 8:
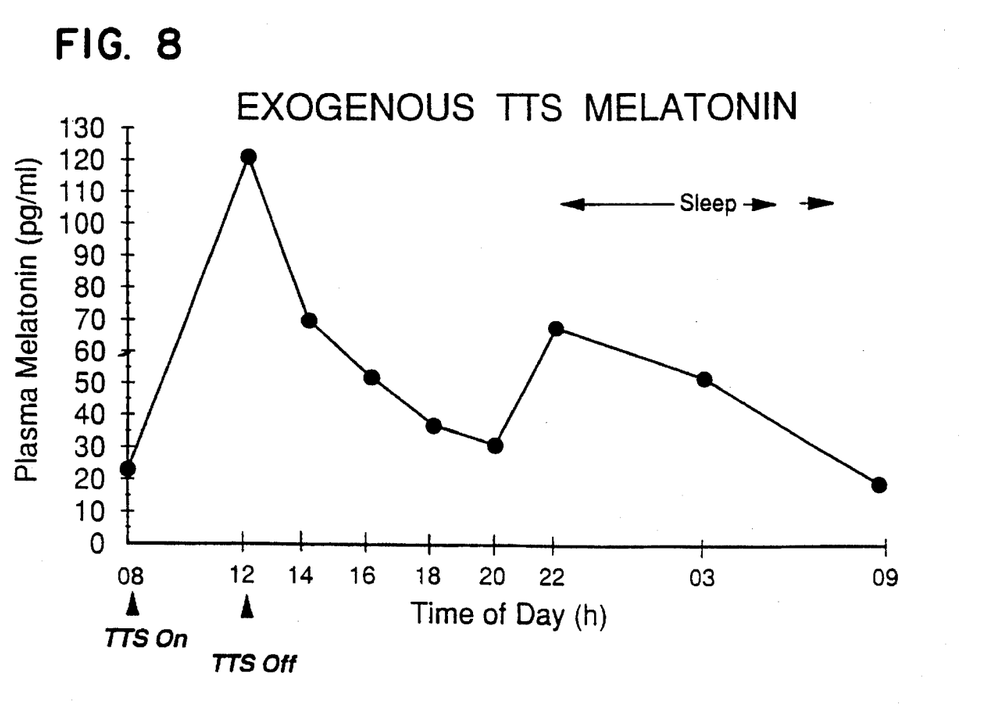

The results are shown in FIGS. 5–8, which present the plasma concentration of melatonin as a result of the exogenous delivery of melatonin from the transdermal device (FIGS. 6 and 8), in comparison with the endogenous control baseline concentrations (FIGS. 5 and 7). FIGS. 6 and 8 illustrate the increasing melatonin concentration as a result of delivery of melatonin from the transdermal device, the concentration peaking at about the point where the device is removed and followed by a decrease to normal endogenous levels ("TTS"= transdermal therapeutic system or device). They additionally show a second curve peaking at about 10:00 p.m. (22:00), which is consonant with the natural endogenous production of melatonin by each of the two individuals.

Having thus generally described the present invention and described certain specific embodiments thereof including the embodiments that the applicants consider the best mode of practicing their invention, it will be readily apparent that various modifications to the invention may be made by workers skilled in the art without departing from the scope of this invention which is limited only by the following claims.

What is claimed is:

1. A device for the transdermal administration, at a therapeutically effective rate, of melatonin, which device comprises:
   (a) a reservoir comprising a therapeutically effective amount of melatonin and a skin permeation-enhancing amount of a monoglyceride or mixture of monofilycerides of fatty acids with a total monoesters content of at least 51%;
   (b) a backing impermeable to the melatonin on the skin-distal surface of the reservoir; and
   (c) means for maintaining the reservoir in melatonin- and permeation enhancer-transmitting relation with the skin.

2. A device according to claim 1 wherein the permeation enhancer is glycerol monooleate or glycerol monolinoleate.

3. A device according to claim 1 wherein the melatonin is administered through the skin at a rate of at least 0.1 µg/hour for a predetermined period of time.

4. A device according to claim 3 wherein the predetermined period of time is about 1 to 6 hours.

5. A device according to claim 1 wherein the permeation enhancer is glycerol monooleate and the matrix comprises ethylene vinyl acetate copolymer having from about 9% to 60% vinyl acetate.

6. A device according to claim 5 wherein the means for maintaining the reservoir in relation with the skin comprises an in-line adhesive layer on the skin-proximal surface of the reservoir.

7. A device for the transdermal administration, at a therapeutically effective rate, of melatonin, which device comprises:
   (a) a first reservoir comprising a therapeutically effective amount of melatonin and a skin permeation-enhancing amount of a monofilyceride or mixture of monoglycerides of fatty acids with a total monoesters content of at least 51%;
   (b) a second reservoir comprising an excess of the permeation enhancer and being substantially free of melatonin;
   (c) a rate-controlling membrane between the first reservoir and the second reservoir;
   (d) a backing impermeable to melatonin on the skin-distal surface of the second reservoir; and
   (e) means for maintaining the first and second reservoirs in melatonin- and permeation enhancer-transmitting relation with the skin.

8. A device according to claim 7 wherein the melatonin is administered through the skin at a rate of at least 0.1 µg/hour for a predetermined period of time.

9. A device according to claim 8 wherein the predetermined period of time is about 1 to 6 hours.

10. A device according to claim 7 wherein the means for maintaining the reservoirs in relation with the skin comprises an in-line adhesive layer on the skin-proximal surface of the first reservoir.

11. A device according to claim 7 wherein the first reservoir also is an adhesive layer which functions as the means for maintaining the reservoirs in relation with the skin.

12. A device according to claim 7 wherein the permeation enhancer is glycerol monooleate or glycerol monolinoleate.

13. A method for the transdermal administration of melatonin, which method comprises:
   (a) administering melatonin at a therapeutically effective rate to an area of skin; and
   (b) simultaneously administering a monoglyceride or mixture of monoglycerides of fatty acids with a total monoesters content of at least 51% to the area of skin at a rate which is sufficient to substantially increase the permeability of the area to the melatonin.

14. A method according to claim 13 wherein the permeation enhancer is glycerol monooleate or glycerol monolinoleate.

15. A method according to claim 13 wherein the melatonin is administered through the skin at a rate of at least 0.1 µg/hour for a predetermined period of time.

16. A method according to claim 15 wherein the predetermined period of time is about 1 to 6 hours.

17. A method for providing uninterrupted sleep to a person having fragmented sleep, the method comprising the step of placing a melatonin transdermal delivery device onto the skin of a person prior to the bedtime of the person, the melatonin transdermal delivery device comprising:
   (a) a reservoir comprising melatonin in an amount sufficient to provide a hypnotic effect for a predetermined period of time and a monoglyceride or mixture of monoglycerides of fatty acids with a total monoesters content of at least 51% in a skin permeation-enhancing amount;
   (b) an impermeable backing on the skin-distal surface of the reservoir; and
   (c) means for maintaining the reservoir in melatonin- and permeation enhancer-transmitting relation with the skin.

18. A method according to claim 17 wherein the permeation enhancer is glycerol monooleate or glycerol monolinoleate.

19. A method according to claim 17 wherein the melatonin is administered through the skin at a rate of at least 0.1 µg/hour for the predetermined period of time.

20. A method according to claim 19 wherein the predetermined period of time is about 1 to 6 hours.

21. A method according to claim 17 wherein the permeation enhancer is glycerol monooleate and the matrix comprises ethylene vinyl acetate copolymer having from about 9% to 60% vinyl acetate.

22. A method according to claim 21 wherein the means for maintaining the reservoir in relation with the skin comprises an in-line adhesive layer on the skin-proximal surface of the reservoir.

23. A method for providing uninterrupted sleep to a person having fragmented sleep, the method comprising the step of placing a melatonin transdermal delivery device onto the skin of a person prior to the bedtime of the person, the melatonin transdermal delivery device comprising:

(a) a first reservoir comprising melatonin in an amount sufficient to provide a hypnotic effect for a predetermined period of time and a monoglyceride or mixture of monoglycerides of fatty acids with a itotal monoesters content of at least 51% in a skin permeation-enhancing amount;

(b) a second reservoir comprising an excess of the permeation enhancer and substantially free of melatonin;

(c) a rate-controlling membrane between the first reservoir and the second reservoir;

(d) an impermeable backing on the skin-distal surface of the second reservoir; and (e) means for maintaining the first and second reservoir in melatonin- and permeation enhancer-transmitting relation with the skin.

24. A method according to claim 23 wherein the melatonin is administered through the skin at a rate of at least 0.1 µg/hour for a predetermined period of time.

25. A method according to claim 24 wherein the predetermined period of time is about 1 to 6 hours.

26. A method according to claim 23 wherein the means for maintaining the reservoirs in relation with the skin comprises an in-line adhesive layer on the skin-proximal surface of the first reservoir.

27. A method according to claim 23 wherein the first reservoir also is an adhesive layer which functions as the means for maintaining the reservoirs in relation with the skin.

28. A device according to claim 23 wherein the permeation enhancer is glycerol monooleate or glycerol monolinoleate.

29. A device for the transdermal administration, at a therapeutically effective rate, of melatonin, which device comprises:

(a) a reservoir comprising a therapeutically effective amount of melatonin and a skin permeation-enhancing amount of a monoglyceride or mixture of monoglycerides of fatty acids with a total monoesters content of at least 51%;

(b) a backing impermeable to the melatonin on the skin-distal surface of the reservoir; and (c) means for maintaining the reservoir in melatonin- and permeation enhancer-transmitting relation with the skin; wherein the melatonin is administered through the skin at a rate of about 0.1–200 µg/hr for a predetermined period of time.

30. A device for the transdermal administration, at a therapeutically effective rate, of melatonin, which device comprises:

(a) a first reservoir comprising a therapeutically effective amount of melatonin and a skin permeation-enhancing amount of a monoglyceride or mixture of monoglycerides of fatty acids with a total monoesters content of at least 51%;

(b) a second reservoir comprising an excess of the permeation enhancer and being substantially free of melatonin;

(c) a rate-controlling membrane between the first reservoir and the second reservoir;

(d) a backing impermeable to melatonin on the skin-distal surface of the second reservoir; and (e) means for maintaining the first and second reservoirs in melatonin- and permeation enhancer-transmitting relation with the skin; wherein the melatonin is administered through the skin at a rate of about 0.1–200 µg/hr for a predetermined period of time.

31. The device according to claims 29 or 30 wherein the predetermined period of time is about 1 to 6 hours.

32. A method for the transdermal administration of melatonin, which method comprises:

(a) administering melatonin to an area of skin; and (b) simultaneously administering a permeation enhancer to the area of skin at a rate which is sufficient to substantially increase the permeability of the area to the melatonin, wherein the melatonin is delivered through the skin at a rate of about 0.1–200 µg/hr for a predetermined period of time.

33. The method of claim 32 wherein the predetermined period of time is about 1 to 6 hours.

* * * * *

UNITED STATES PATENT AND TRADEMARK OFFICE
CERTIFICATE OF CORRECTION

PATENT NO. : 5,508,039
DATED : April 16, 1996
INVENTOR(S) : F. Eugene Yates, Lina T. Taskovich, Su I. Yum and Nieves M. Crisologo It is certified that error appears in the above-indentified patent and that said Letters Patent is hereby corrected as shown below:

In claim 1, at column 13, lines 36-37, "monofilycerides" should read --monoglycerides--; claim 7, at column 13, line 64, "monofilyceride" should read --monoglyceride--; and claim 23, at column 15, line 17, should read --total-- instead of "itotal".

Signed and Sealed this

Twenty-third Day of July, 1996

Attest:

BRUCE LEHMAN

Attesting Officer     Commissioner of Patents and Trademarks